United States Patent
Macfarlane et al.

(10) Patent No.: US 7,783,336 B2
(45) Date of Patent: Aug. 24, 2010

(54) SUBCUTANEOUS BIOPSY CAVITY MARKER DEVICE

(75) Inventors: K. Angela Macfarlane, Woodside, CA (US); Sascha Zarins, Los Gatos, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 741 days.

(21) Appl. No.: 10/856,489

(22) Filed: May 28, 2004

(65) Prior Publication Data

US 2005/0020916 A1 Jan. 27, 2005

Related U.S. Application Data

(60) Provisional application No. 60/476,533, filed on Jun. 6, 2003.

(51) Int. Cl.
*A61N 5/00* (2006.01)
(52) U.S. Cl. .......................................... 600/407; 600/3
(58) Field of Classification Search ................ 600/431, 600/426, 1, 3, 4, 7, 8, 434, 407, 414, 423, 600/437; 606/151, 144, 116; 623/1.34, 1, 623/2, 12; 424/423
See application file for complete search history.

(56) References Cited

U.S. PATENT DOCUMENTS

| | | | | |
|---|---|---|---|---|
| 3,297,033 | A | * | 1/1967 | Schmitt et. al. ............. 606/230 |
| 4,249,539 | A | | 2/1981 | Vilkomerson et al. |
| 5,076,278 | A | | 12/1991 | Vilkomerson et al. |
| 5,201,314 | A | * | 4/1993 | Bosley et al. ............... 600/458 |
| 5,488,951 | A | | 2/1996 | Bauer et al. |
| 6,144,875 | A | | 11/2000 | Schweikard et al. |
| 6,228,055 | B1 | * | 5/2001 | Foerster et al. ............. 604/116 |
| 2002/0035324 | A1 | * | 3/2002 | Sirimanne et al. ........... 600/431 |

FOREIGN PATENT DOCUMENTS

| | | |
|---|---|---|
| JP | 2002-52079 | 2/2002 |
| WO | 01/00101 | 1/2001 |
| WO | WO01/00101 | 1/2001 |

* cited by examiner

*Primary Examiner*—Brian Casler
*Assistant Examiner*—Elmer Chao

(57) ABSTRACT

A marking device for identifying a subcutaneous biopsy cavity having a first nonabsorbable marker element detectable by a first imaging modality and a second nonabsorbable marker element detectable by a second imaging modality but not detectable by the first imaging modality.

20 Claims, 3 Drawing Sheets

SUBCUTANEOUS BIOPSY CAVITY MARKER DEVICE

This application claims priority to U.S. Provisional App. Ser. No. 60/476,533 filed Jun. 6, 2003, the contents of which are hereby incorporated by reference.

FIELD OF THE INVENTION

This invention relates to nonabsorbable biopsy cavity maker devices and methods for identifying such devices in a subcutaneous biopsy cavity, including a breast biopsy cavity.

BACKGROUND OF THE INVENTION

Invasive breast cancer, the most common nonskin cancer in American women, was diagnosed in approximately 184,000 women in the United States in 2000, and let to approximately 41,000 deaths (Nancy E. Davidson. 2001. "Breast Cancer", Section 12 Part VII In *Scientific American Medicine*. Edward Rubenstein and Daniel D. Federman eds., Scientific American, Inc.: New York, N.Y.). Current guidelines for breast cancer screening recommended by the American Cancer Society and the National Cancer Institute include monthly breast self examination for all women older than 20 years and annual mammography for women older than 40 years who are at standard risk for breast cancer. For those at higher risk, current practice advocates that mammographic screening begin at 25 years of age or five years earlier than the age of the person with the earliest diagnosis of breast cancer in the immediate or extended family.

Breast cancer may present as architectural changes or microcalcifications on a mammogram, or by clinical symptoms, such as a palpable mass, nipple discharge, or skin or nipple changes. Regardless of whether the patient is symptomatic or asymptomatic, a histologic examination of the suspect tissue is mandatory to establish a diagnosis. Open incisional or excisional biopsies were commonly performed in the past to obtain tissue samples. The modern trend relies on fine-needle aspiration, core-needle biopsy, or other image guided or non-image guided percutaneous procedures, e.g., vacuum assisted biopsy using the MAMMOTOME® breast biopsy system (Ethicon Endo-Surgery, Inc., Cincinnati, Ohio), to obtain a sample of cells or tissue for diagnosis.

After any given biopsy procedure, a subsequent examination of the biopsy site is often desirable. For example, if the initial biopsy only partially removed the suspect tissue, and a malignant lesion is subsequently diagnosed, re-excision of the original biopsy site is indicated. Identification of a biopsy site is also helpful during patient follow-up examinations for reoccurrence. Thus, there is a need to determine the location, most importantly the center, as well as the orientation and margins of the subcutaneous tissue cavity from which the suspect lesion is removed.

Prior methods of marking biopsy cavities utilize one or more tissue marking clips as the biopsy site marking device. One representative marking apparatus is the MICROMARK™ II tissue marker (Biopsis Medical, Inc., Irvine, Calif.). Among other concerns, deployment of the MICROMARK™ II tissue maker is unreliable, the marker device often failing to properly attach to the cavity wall. Furthermore, because clip attachment occurs to the side, not the center of the cavity, spatial orientation and position of the cavity is difficult if not impossible during follow-up examination. Moreover, during the stereotactic breast biopsy procedure, the breast is under compression when the marking clip is placed. Upon release of the compressive force, the clip will migrate relative to the biopsy void, and the orientation as well as the location of the margins of the cavity are usually lost.

Other biopsy markers that attempt to minimize migration, e.g., after tissue is decompressed, are described in U.S. Pat. No. 6,161,034 and U.S. Pat. No. 6,347,241, both to Burbank et al.; U.S. Pat. No. 6,270,464 to Fulton, III et al.; and U.S. Pat. No. 6,350,244 and WO 01/62135, both to Fisher.

Burbank et al. describes chemical preparations of collagen or gelatin having a visible marker such as carbon particles or a dye that are introduced into biopsy cavities. The markers are imageable by mammography, fluoroscopy, CT, or MRI.

Fulton, III et al. depicts a swellable marker that may be palpably harder after delivery into the biopsy cavity. The marker is imageable by mammography, ultrasound, or MRI.

In U.S. Pat. No. 6,350,244 and WO 01/62135, Fisher describes markers that are hollow spheres made from polylactic acid. The spheres are filled with iodine or other radiopaque material to make them imageable by available radiographic techniques such as x-ray and/or ultrasound. Multiple markers are introduced to fill the biopsy cavity.

In U.S. Pat. No. 6,347,241, Burbank et al. describes a marker body that includes a pre-shaped pellet formed of bioabsorbable material having a plurality of gas bubbles dispersed therein which are configured to facilitate ultrasonic observation of the pellet at a biopsy site within a patient and having an X-ray detectable element of specific predetermined non-biological configuration embedded therein.

Although the above mentioned marker devices address some of the problems associated with clip-type markers, the problem of prolonged monitoring of a biopsy site still remains. Thus, it would be of considerable medical benefit to be able to permanently mark the location of a biopsy cavity, especially after a percutaneous biopsy procedure.

SUMMARY OF THE INVENTION

The present invention is a subcutaneous biopsy cavity marking device that permanently remains within the biopsy cavity after deployment, and which has one or more marker elements that allows identification of the biopsy cavity center, orientation, or margin, using various imaging modalities.

The marking device generally includes a first marker element and a second nonabsorbable marker element. The first marker element is detectable by a first imaging modality. The second marker element is detectable by a second imaging modality that differs from the first imaging modality. In one embodiment, the first imaging modality usually does not visualize the second marker element. However, if it is visualized, the second marker element will have a configuration such that it is distinguishable from naturally occurring artifacts, and is configured so that it does not obscure the presence of any tissue pathology or confound the reading of any imaging study using the first modality. In a preferred variation, x-ray is the first imaging modality and ultrasonography is the second imaging modality.

The first marker element may be variously shaped, and made from materials such as gold, iridium, nickel, rhodium, silver, stainless steel, tantalum, titanium, and alloys thereof. A radiopaque additive may also be coated on or incorporated into the first marker element to enhance the radiopacity of the element.

The second marker element may also have various configurations and is formed from nonabsorbable materials such as fluoropolymers, polyester or polyester mixtures, polypropylene, and nylon or nylon mixtures. An echogenic coating may also be provided on the second marker element to enhance its detection by ultrasound imaging.

In addition to being nonabsorbable, in one embodiment of the invention, the marking devices are nonpalpable. In a further embodiment, pharmaceutical agents such as hemostatic, analgesic, or anesthetic substances may also be incorporated into either the first or second marker elements or both. In some cases, it may also be desirable to form the marker device to emit therapeutic radiation to treat any diseased tissue remaining within the biopsy cavity.

BRIEF DESCRIPTION OF THE FIGURES

FIG. 1A shows a spherical biopsy cavity marker device according to one variation of the invention.

FIG. 1B shows a multi-faced biopsy cavity marker device according to another variation of the invention.

FIG. 1C shows a cylindrical biopsy cavity marker device according to another variation of the invention.

FIG. 1D shows a knotted suture biopsy cavity marker device according to yet another variation of the invention.

FIG. 1E is a biopsy cavity marker device having a looped arrangement according to another variation of the invention.

FIG. 1F is a biopsy cavity marker having a layered configuration according to another variation of the invention.

FIG. 1G is a biopsy cavity marker having a rolled configuration according to another variation of the invention.

DETAILED DESCRIPTION OF THE INVENTION

The biopsy marker devices of this invention may take various forms, but are generally configured to have a size and shape appropriate for identifying a biopsy cavity, e.g., a breast biopsy cavity. Once within the biopsy cavity, the marker device allows localization, as well as orientation and identification of the cavity margins. The marker devices are nonabsorbable, allowing long-term follow-up examination of the biopsy site if desired. When the marker devices permanently remain within the biopsy cavities, they are preferably formed to be nonpalpable.

The reluctance to use nonabsorbable biopsy cavity markers may arise from the notion that a foreign body reaction may be generated by the prolonged presence of the marker in the cavity, leading to fibrosis. The area of induration would most likely be palpable and thus, undesirable to the patient. Therefore, the marker devices of this invention will be constructed from biocompatible materials which do not produce any detrimental effect (such as fibrosis or other palpable or noticeable condition) on the patient.

Furthermore, a need for nonabsorbable markers was not present in the past because most patients with nonpalpable suspicious lesions underwent wire localization biopsy which is an open incisional or excisional biopsy. If a malignancy was diagnosed from the specimen, re-excision was accomplished by opening the previous incision. However, with the increasing popularity of percutaneous biopsy procedures and breast-sparing surgery, biopsy cavities are decreasing in size, making them difficult to detect on follow-up imaging. Long-term follow-up for suspicious lesions that are found to be benign after percutaneous biopsy is difficult if biopsy cavity markers are generally bioabsorbable, and degrade after a few months. The biopsy cavity markers of this invention are nonabsorbable, and thus are detectable for follow-up over any desired period of time.

The marker devices may be introduced into biopsy cavities by various suitable percutaneous access devices, e.g., as described in U.S. Pat. No. 6,356,782 and U.S. Pat. No. 6,371,904 to Sirimanne et al., and U.S. Publication No. 2003/0050571 to Zarins et al which are herein incorporate by reference in their entireties.

Figure 1A:
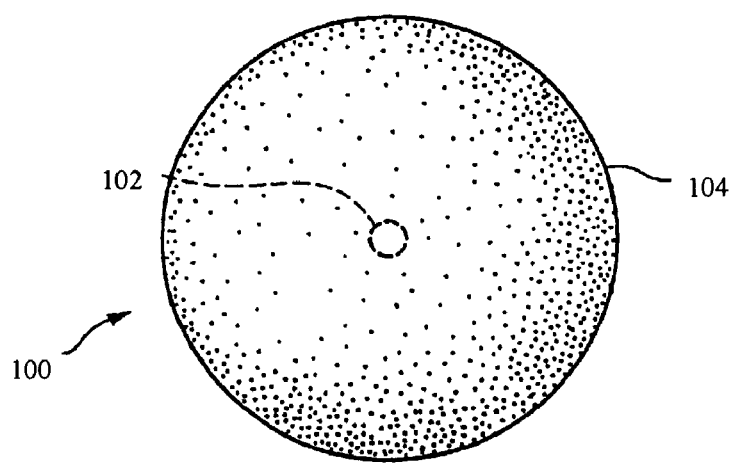
FIGS. 1A-1G illustrate various configurations of the biopsy cavity marker devices.
Figure 1B:
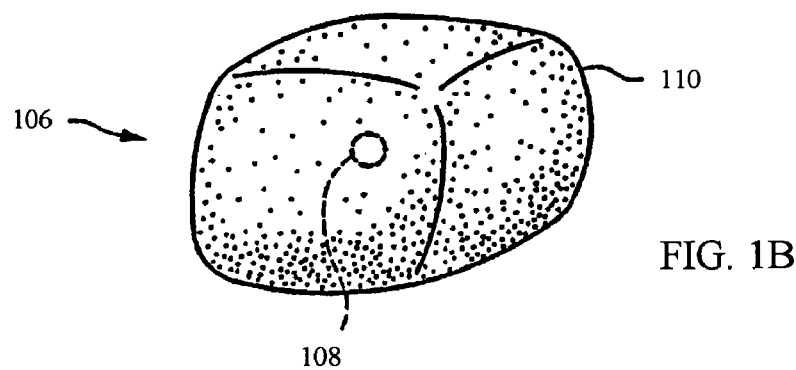
Figure 1C:
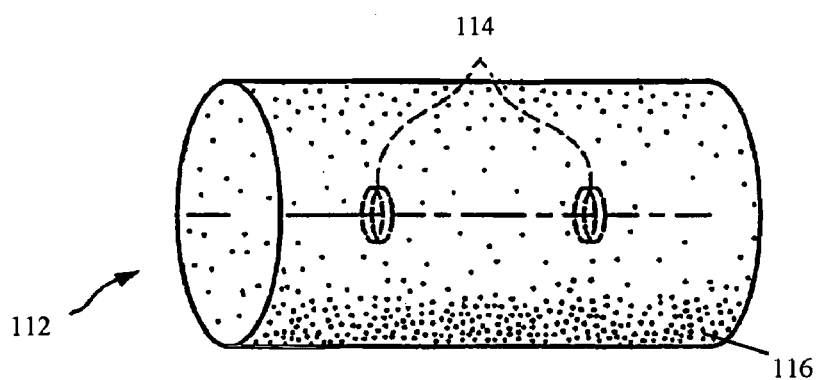

FIGS. 1A-1G show various configurations of subcutaneous cavity marking devices of the present invention. In the Figures, the marker device 100 is displayed as having either a generally spherical body (FIG. 1A), a multi-faced body 106 (FIG. 1B), or a generally cylindrical body 112 (FIG. 1C). In addition, it is within the scope of this invention for the body to assume a variety of other shapes. For example, the marker device may be configured to have conical or ellipsoidal shapes, substantially planar surfaces, such as polyhedric (i.e., cubic, tetrahedral) or prismatic forms, and the like. Furthermore, the nonabsorbable materials that make up the marker devices may be designed to have a knotted structure (FIG. 1D) or a looped (FIG. E), layered (FIG. 1F), or rolled (FIG. 1G) arrangement.

The particular marker device may be of any shape, as well as size, so long as the marker is distinguishable from tissue pathology, e.g., microcalcifications, or from anatomically occurring artifacts, and will typically be chosen to best match the biopsy cavity dimensions. Marker devices having a fixed geometry, e.g., rolls or cubes, are preferable because their geometry is more readily distinguishable from tissue pathology and anatomically occurring artifacts.

The subcutaneous biopsy cavity markers generally include a first marker element (e.g., 102, 108, 114, 118, 122, 126, 130) and a second marker element (e.g., 104, 110, 116, 120, 124, 128, 132). The first marker element is detectable by a first imaging modality. The second marker element is detectable by a second imaging modality but preferably is not detectable by the first imaging modality. By "not detectable" we mean that under the first imaging modality there is no significant visualization of the second marker element. The second imaging modality will typically provide a more efficient outpatient follow-up process because the imaging device is portable, and readily available in most surgical oncology offices. Preferably, the first imaging modality is x-ray and the second imaging modality is ultrasonography.

The first imaging modality is usually a radiographic imaging modality. For example, an x-ray such as a mammogram may be taken, or an image may be obtained using computed tomography (CT) for fluoroscopy. Besides radiography, magnetic resonance imaging (MRI) may also be performed. In a preferred variation, mammography is used as the first imaging modality. By using ultrasonography as the second imaging modality, which will also be employed for long-term follow-up, total radiation exposure to the patient is decreased. In addition, the increasing use of hand-held or portable ultrasound devices by surgeons provides convenient long-term outpatient follow-up without referral back to a radiologist.

The first marker element 102, 108, 114, 118, 122, 126, 130 may be confined within the structure of the second marker element 104, 110, 116, 120, 124, 128, 132, as seen in FIGS. 1A-1C, or may wrap around a portion of the second marker element, as seen in FIGS. 1D-1G. The placement of the marker elements in relation to one another may vary according to such factors as type of tissue biopsied, dimensions of the biopsy cavity, number of first marker elements employed, and physician preference, so long as the center of the cavity, and the orientation and margins of the cavity can generally be identified.

Figure 1D:
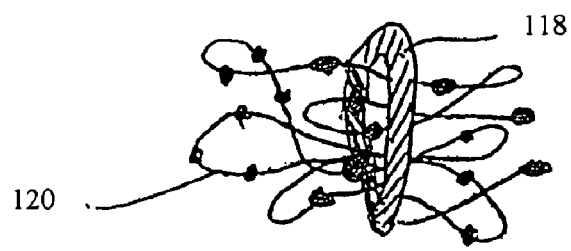
Figure 1E:
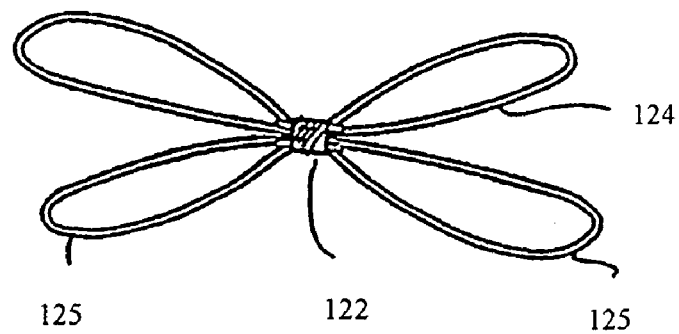
Figure 1F:
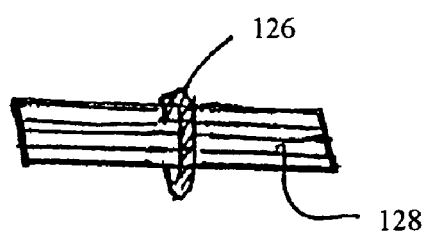
Figure 1G:
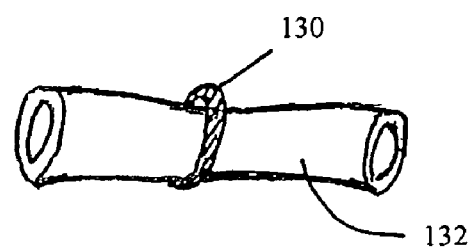
Figure 2A:
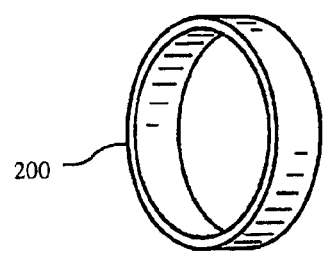
FIG. 2A shows a first marker element having a ring shape according to one variation of the invention.
Figure 2B:
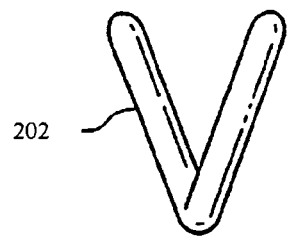
FIG. 2B shows a first marker element having a barbed ('V') shape according to another variation of the invention.
Figure 2C:
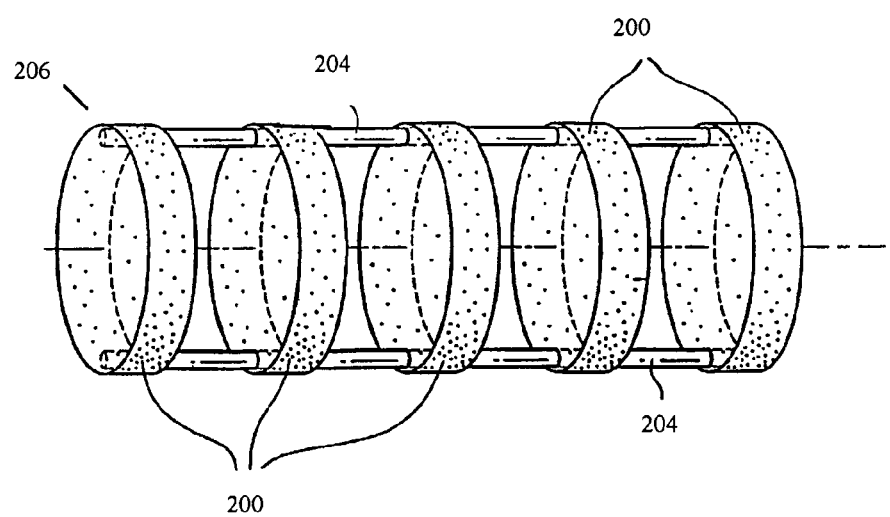
FIG. 2C shows a first marker element having a plurality of ring-shaped components connected by a joining element according to another aspect of the invention.

The first marker element 102, 108, 114, 118, 122, 126, 130 may be spherical (FIGS. 1A and 1B), ring-shaped (FIGS. 1C-1G, 2A), or barbed in a 'V' configuration (FIG. 2B). Although the Figures illustrate only three configurations for the first marker elements, the invention contemplates other configurations that allow adequate detection of the biopsy cavity as described above. Furthermore, a plurality of first marker elements may be included in the marking device if so indicated or desired. In one variation, as seen in FIG. 2C, a plurality of rings 200 are connected by a joining member 204, e.g., by an adhesive or soldering, to form a first marker element 206.

In one embodiment, the first marker element 102, 108, 114, 118, 122, 126, 130 may be made from nonabsorbable, metallic materials including, but not limited to, gold; iridium; nickel; rhodium; silver; stainless steel; tantalum; titanium; and alloys thereof. In a preferred variation, the first marker element is made from titanium. However, the first marker element may be made from any type of materials, so long as it is biocompatible and nonabsorbable.

If desired, the radiopacity of the first marker element may be enhanced by adding a radiopaque additive coating to the marker. Suitable radiopaque additives include elements such as barium-containing compounds, bismuth-containing compounds, powdered tantalum, powdered tungsten, barium carbonate, bismuth oxide, and barium sulfate.

The second marker element may also be provided in various configurations. For example, in one variation, the second marker element 120 is formed from knotted surgical suture. As seen in FIG. 1D, the first marker element 118 is a ring that wraps around the second marker element 120 in the form of a knotted mass. In another variation, the second marker element is a looped arrangement of suture 124 (FIG. 1E). The suture material is looped through the first marker element 122, also a ring structure, to form a pair of opposing loops 125. In yet a further variation, the second marker element is a layered arrangement of nonabsorbable, echogenic, sheet or mesh-like material 128 centrally fastened together with a ring-shaped first marker element 126 (FIG. 1F). In another variation, as seen in FIG. 1G, the second marker element is in a rolled configuration 132. The roll 132 is passed through and secured by a first marker element, ring 130. In some instances, a plurality of second marker elements may be deployed to fill the biopsy cavity.

The second marker element may be made from biocompatible, nonabsorbable materials including, but not limited to, polymers such as fluoropolymers; polyester (e.g., Reemay® spunbond polyester, Dacron® polyester fibers) and polyester mixtures (e.g., mixtures of polyester and rayon); polypropylene; and nylon and nylon mixtures. If desired, the second marker element may be made from a resilient material. The composition of the second marker element may vary so long as the material it is made from is biocompatible, nonabsorbable, detectable by ultrasound (echogenic), and nonpalpable when placed into a biopsy cavity. These nonabsorbable materials may be subjected to processes such as lyophilization or sintering to bulk them and/or have them capture air. Die-cut second marker elements may be produced using materials treated in this matter. For example, instead of layering or rolling the nonabsorbable material as shown in FIGS. 1F an 1G, respectively, a structure that resembles the shape and size of the layered or rolled marker elements may be cut out from nonabsorbable material that has been lyophilized.

To enhance detection by ultrasound, the second marker element may be coated with an echogenic substance. One such substance is the ECHO-COAT® coating (STS Biopolymers, Henrietta, N.Y.). Echogenic coatings provide the coated marker element with an acoustically reflective interface and a large acoustical impedance differential.

Pharmaceutical agents such as hemostatic, analgesic, or anesthetic agents may also be incorporated into the first and/or second marker elements of the device. Hemostasis-promoting agents help to prevent the formation of hematomas and may also help to promote the healing process. The first and/or second marker elements of the biopsy cavity marker device may also be formed to emit therapeutic radiation to treat any cancerous tissue remaining in the margin of the biopsy cavity.

The biopsy cavity marker devices of the present invention may be inserted into a biopsy cavity by any known means. For example, a marker (or several markers) may be inserted into a syringe type applicator and injected into a biopsy cavity.

All publications, patents, and patent applications cited herein are hereby incorporated by reference in their entirety for all purposes to the same extent as if each individual publication, patent, or patent application were specifically and individually indicated to be so incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims.

What is claimed is:

1. A marking device for identifying a subcutaneous biopsy cavity comprising:
   a first nonabsorbable marker element detectable by a first imaging modality, which is a radiographic imaging modality; and
   a second nonabsorbable marker element detectable by a second imaging modality, which is ultrasonography, but not detectable by said first imaging modality,
   wherein the second marker element extends generally along an axis and the first marker element is radiopaque, encircles a portion of the second marker element, and lies in a plane that is generally perpendicular to the axis of the second marker element.

2. The marking device of claim 1 wherein said device is nonpalpable.

3. The marking device of claim 1 wherein said first marker element comprises a material selected from a group consisting of gold; iridium; nickel; rhodium; silver; stainless steel; tantalum; titanium; and alloys thereof.

4. The marking device of claim 1 wherein said first marker element comprises titanium.

5. The marking device of claim 1 wherein said first marker element comprises a radiopaque additive.

6. The marking device of claim 5 wherein said radiopaque additive is selected from the group consisting of barium-containing compounds, bismuth-containing compounds, powdered tantalum, powdered tungsten, barium carbonate, bismuth oxide, and barium sulfate.

7. The marking device of claim 1 wherein said first marker element is ring-shaped.

8. The marking device of claim 1 wherein said radiographic imaging modality is an x-ray.

9. The marking device of claim 8 wherein said x-ray is a mammogram.

10. The marking device of claim 1 wherein said first imaging modality is mammography.

11. The marking device of claim 1 wherein said second marker element comprises a material selected from the group consisting of fluoropolymers, polyester and polyester mixtures, polypropylene, and nylon and nylon mixtures.

12. The marking device of claim 1 wherein said second marker element comprises an echogenic coating.

13. The marking device of claim 1 wherein said second marker element comprises a knotted suture.

14. The marking device of claim 1 wherein said second marker element comprises a looped arrangement of suture.

15. The marking device of claim 1 wherein said second marker element comprises a layered arrangement of sheet or mesh-like material.

16. The marking device of claim 1 wherein said second marker element has a rolled configuration.

17. The marking device of claim 1 wherein said second marker element has a geometry distinguishable from an anatomically occurring artifact or tissue pathology.

18. The marking device of claim 1 wherein said second nonabsorbable marker element is resilient.

19. The marking device of claim 1 wherein said first marker element comprises a metal and said second nonabsorbable marker element comprises a polymer.

20. A method of identifying a subcutaneous biopsy cavity comprising:
    placing a biopsy cavity marking device into said biopsy cavity, the biopsy cavity marking device having a first nonabsorbable marker element and a second nonabsorbable marker element, wherein the second marker element extends generally along an axis and the first marker element is radiopaque, encircles a portion of the second marker element, and lies in a plane that is generally perpendicular to the axis of the second marker element;
    detecting said first marker using a first imaging modality, which is a radiographic imaging modality; and
    detecting said second marker element by a second imaging modality, which is ultrasonography, that differs from said first imaging modality, and said second marker element being undetectable by said first imaging modality, wherein said biopsy cavity marking device is nonpalpable.

* * * * *